(12) United States Patent
Rossi et al.

(10) Patent No.: US 10,753,926 B2
(45) Date of Patent: Aug. 25, 2020

(54) MACHINE AND METHOD FOR AUTOMATED IN VITRO ANALYTE DETECTION BY MEANS OF CHROMATIC SPECTRAL DECOMPOSITION OF AN OPTICAL RESPONSE

(71) Applicant: BIOMÉRIEUX, Marcy L'étoile (FR)

(72) Inventors: Veronica Lucia Rossi, Florence (IT); Giuseppe Ferorelli, Florence (IT); Antonio Sanesi, Florence (IT); Giuseppe Ubaldini, Bagno A Ripoli (IT)

(73) Assignee: BIOMÉRIEUX, Marcy l'Étoile (FR)

( * ) Notice: Subject to any disclaimer, the term of this patent is extended or adjusted under 35 U.S.C. 154(b) by 309 days.

(21) Appl. No.: 15/567,447

(22) PCT Filed: Apr. 28, 2016

(86) PCT No.: PCT/FR2016/050996
§ 371 (c)(1),
(2) Date: Oct. 18, 2017

(87) PCT Pub. No.: WO2016/174356
PCT Pub. Date: Nov. 3, 2016

(65) Prior Publication Data
US 2018/0106788 A1    Apr. 19, 2018

(30) Foreign Application Priority Data

Apr. 30, 2015 (FR) ...................................... 15 53912

(51) Int. Cl.
*G01N 33/52* (2006.01)
*G01N 21/27* (2006.01)
(Continued)

(52) U.S. Cl.
CPC ........... *G01N 33/52* (2013.01); *A61B 5/0071* (2013.01); *G01N 21/253* (2013.01); *G01N 21/27* (2013.01);
(Continued)

(58) Field of Classification Search
CPC ......... A61B 5/0071; G01N 2021/6417; G01N 2021/6419; G01N 2021/6421;
(Continued)

(56) References Cited

U.S. PATENT DOCUMENTS 5,757,013 A    5/1998 Groger et al.
8,868,156 B1   10/2014 Koops et al.
(Continued)

FOREIGN PATENT DOCUMENTS

EP    0 241 268 A2    10/1987
EP    0 802 413 A2    10/1997
(Continued)

OTHER PUBLICATIONS

International Search Report dated Oct. 24, 2016, for Application No. PCT/FR2016/050996.

*Primary Examiner* — Maureen Wallenhorst
(74) *Attorney, Agent, or Firm* — Oliff PLC

(57) ABSTRACT

A machine for automatic in vitro detection of analytes, the machine being of the type including an optical reader device capable of detecting the optical response of the reaction solution to electromagnetic stimulation using a photoelectric receiver that is carried by a movable carriage of the machine and that moves under automatic control in order to bring the photoelectric receiver into various positions, each corresponding to various respective analysis zones. The photoelectric receiver forms part of a spectrometer capable of delivering a chromatic spectral decomposition of the optical response. Also provided are methods of automatic in vitro
(Continued)

detection and/or quantification of analytes. In one method, a chromatic spectral decomposition of the optical response is acquired and two distinct optical agents are detected separately using the spectral decomposition.

8 Claims, 6 Drawing Sheets

(51) Int. Cl.
    *G01N 21/31* (2006.01)
    *G01N 21/64* (2006.01)
    *G01N 21/77* (2006.01)
    *G01N 35/00* (2006.01)
    *G01N 35/02* (2006.01)
    *A61B 5/00* (2006.01)
    *G01N 21/25* (2006.01)
    *G01N 21/75* (2006.01)

(52) U.S. Cl.
CPC ......... *G01N 21/274* (2013.01); *G01N 21/314* (2013.01); *G01N 21/645* (2013.01); *G01N 21/6428* (2013.01); *G01N 21/77* (2013.01); *G01N 35/00584* (2013.01); *G01N 35/02* (2013.01); *G01N 2021/6417* (2013.01); *G01N 2021/6419* (2013.01); *G01N 2021/6421* (2013.01); *G01N 2021/6441* (2013.01); *G01N 2021/6463* (2013.01); *G01N 2021/755* (2013.01); *G01N 2021/7786* (2013.01); *G01N 2035/00178* (2013.01); *G01N 2201/061* (2013.01)

(58) Field of Classification Search
CPC ... G01N 2021/6441; G01N 2021/6463; G01N 2021/755; G01N 2021/7786; G01N 2035/00178; G01N 21/253; G01N 21/27; G01N 21/274; G01N 21/314; G01N 21/6428; G01N 21/645; G01N 21/77; G01N 2201/061; G01N 33/52; G01N 35/00584; G01N 35/02
USPC ....... 436/43, 164, 165, 171, 172; 422/82.05, 422/82.08, 82.09
See application file for complete search history.

(56) References Cited

U.S. PATENT DOCUMENTS

| 2003/0223059 | A1 | 12/2003 | Li |
| 2007/0086006 | A1 | 4/2007 | Ebersole et al. |
| 2014/0252246 | A1 | 9/2014 | Rossi et al. |

FOREIGN PATENT DOCUMENTS

| EP | 2 853 884 | A1 | | 4/2015 |
| EP | 0 902 772 | A1 | | 8/2015 |
| WO | 97/10506 | A1 | | 3/1997 |
| WO | 97/11354 | A1 | | 3/1997 |
| WO | 2004055502 | A2 | | 7/2004 |
| WO | 2010/009543 | | * | 1/2010 |
| WO | 2010009543 | A1 | | 1/2010 |
| WO | 2013/045807 | | * | 4/2013 |
| WO | 2014045481 | A1 | | 3/2014 |

* cited by examiner

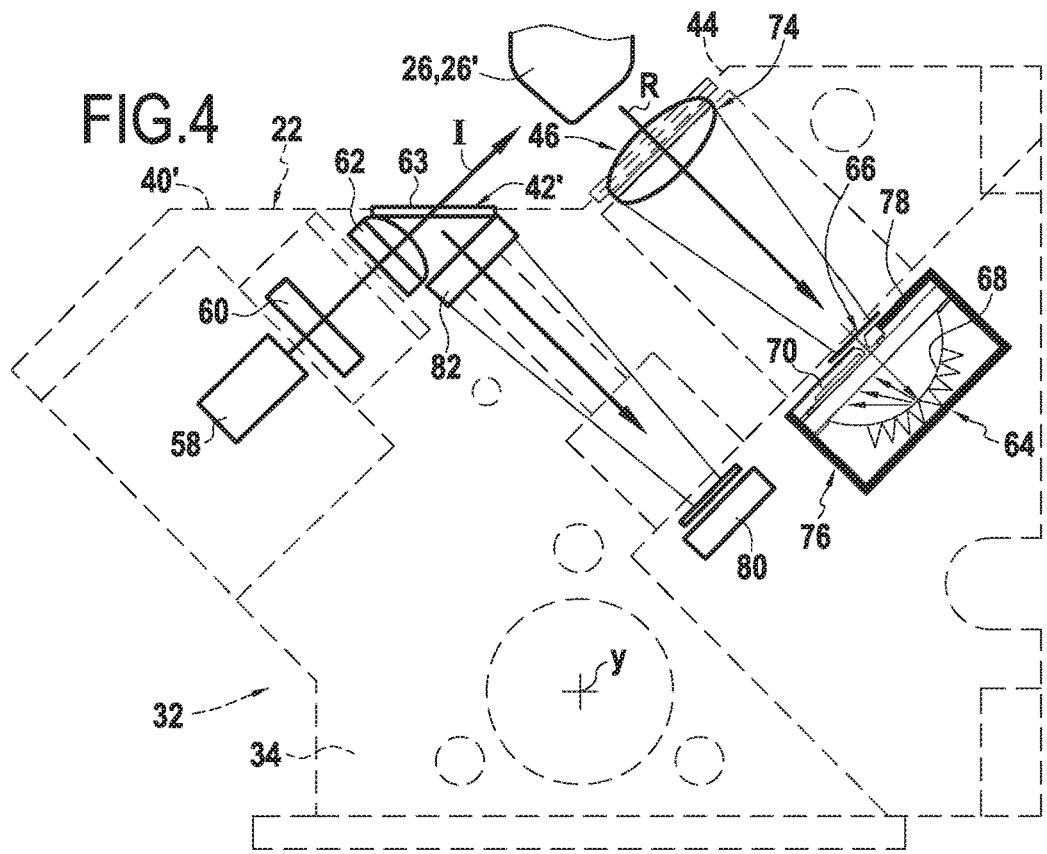
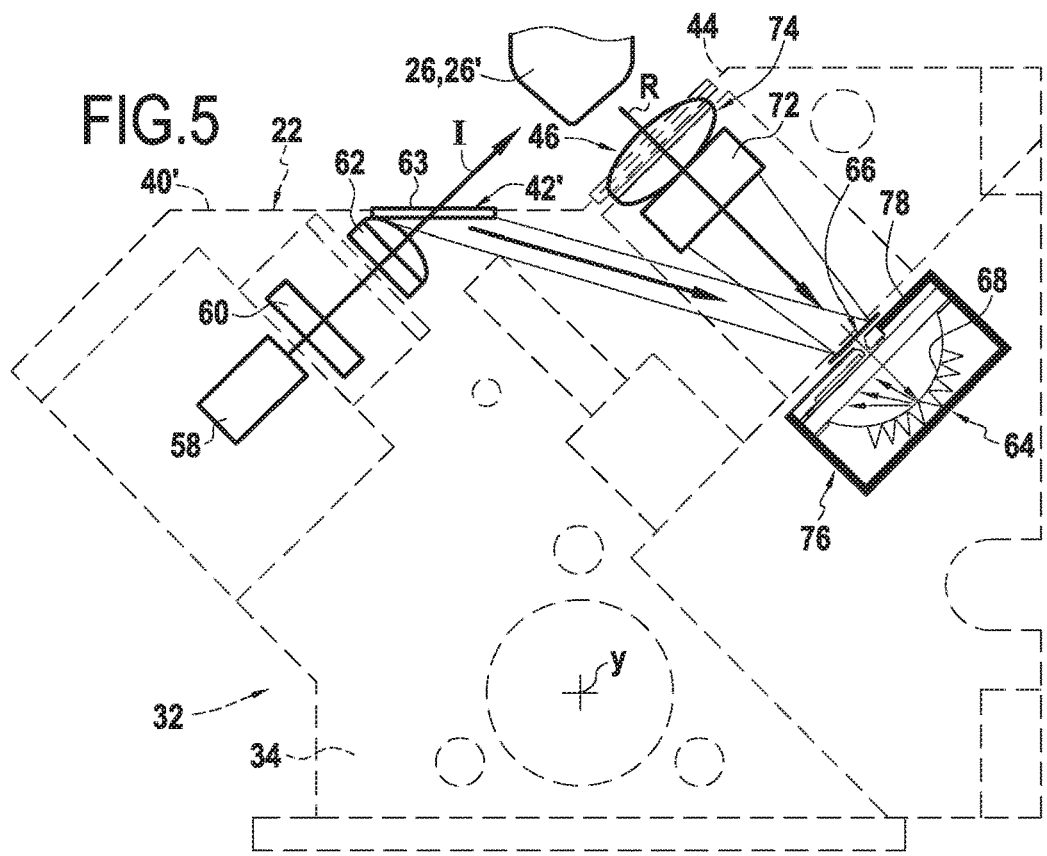

MACHINE AND METHOD FOR AUTOMATED IN VITRO ANALYTE DETECTION BY MEANS OF CHROMATIC SPECTRAL DECOMPOSITION OF AN OPTICAL RESPONSE

The present invention relates to a machine and to methods for detecting and/or quantifying at least one analyte present in a sample, in particular a biological sample, by performing optical analysis, in particular by fluorimetry and/or colorimetry.

The present invention finds an application in automatic in vitro analysis instruments in the clinical field or in the industrial field.

In the clinical field, the analysis may concern a human biological sample (urine, blood, saliva, pus, cerebrospinal fluid, etc.), in order to detect or quantify analytes potentially derived from an external microorganism (bacteria, virus, parasite, antibody, etc.), in particular in the form of immunological tests or molecular biology tests.

In the industrial field, the analysis can relate to a sample of a food, pharmaceutical, or cosmetic product, e.g. for monitoring the microbiological quality of the product in the form of microbiological tests. Such microbiological tests generally verify either sterility (there must be no microorganism present), or the absence of pathogenic bacteria (that could give rise to an infection), or indeed that a commensal bacterium is present but only below a certain threshold (i.e. a bacterium that is normally present in humans and harmless at low concentrations).

The invention can also find an application in the field of dynamic analyses, i.e. analyses in real time, specifically for immunological tests and molecular biology tests in which immunological/biological reactions can be controlled and/or monitored over time.

Such systems or methods for in vitro detection and/or quantification are known, in particular in automatic instruments for in vitro diagnosis by fluorimetry, e.g. as disclosed in Documents EP 0 864 089 B1, EP 0 871 863 B1, EP 0 241 268 A1, U.S. Pat. No. 5,757,013 A, EP 0 802 413, and WO 2004/055502 A2, which employ radiation sources of the type comprising a pulsed light source, a laser lamp, or an arc lamp.

Furthermore, the Applicant sells machines on these principles under the trade name Vidas®, and in particular the machine Vidas® 3 or the machine Vidas® Legacy Blue. Those machines serve in particular to automate the analysis process.

In prior art machines and methods, there are thus to be found:
one or more reception zones each for receiving a sample for analysis;
preparation and automatic reaction means that serve to prepare the sample and cause it to react with reagents in order to form a reaction solution;
a plurality of optical analysis zones, each for receiving a reaction solution obtained by reaction with a sample; and
an optical reader device capable of detecting and/or quantifying the optical response of the reaction solution to electromagnetic stimulation, the optical reader device comprising both at least one source of electromagnetic radiation capable of illuminating an analysis zone, and also a photoelectric receiver arranged to receive light radiation coming from the reaction solution contained in the analysis zone and capable of detecting the optical response of the reaction solution.

In prior art machines, it is known for the optical reader device to be carried by a movable carriage of the machine that is motor-driven and that moves under automatic control in order to bring the optical reader device into various positions, each of which corresponds to a respective analysis zone. Thus, such a machine can use a single movable reader device to analyze the optical response in a plurality of distinct analysis zones in succession, and can do this automatically. It should be observed that in such machines, it is indeed the reader device that moves in order to read the various analysis zones optically, and not the zones that are moved one by one into register with a stationary reader device. This thus requires optical reader devices to be designed that are simple, since they must be movable.

In the state of the art, the machines perform a method for automatic in vitro detection and/or quantification of analytes contained in the samples, which method generally comprises the following steps:
putting the sample into a situation to react with one or more reagents in order to produce directly or indirectly a reaction solution that, when a determined analyte is present in the sample, includes an agent having determined optical properties, in particular fluorescent properties;
illuminating the reaction source with electromagnetic radiation;
detecting the optical response of the reaction solution; and
from the optical response, deducing the presence of and/or quantifying the analyte.

In conventional manner, signals coming from the photodetector means are analyzed by analog or digital processing, in particular using an algorithm for detecting a light intensity at a predetermined frequency/wavelength that is characteristic of the agent that is representative of the presence/quantity of analyte that is to be detected.

For this purpose, use is generally made of a photoelectric sensor, and the optical response of the reaction solution is filtered by an optical filter arranged between the analysis zone and the photoelectric sensor so as to pass light only at one wavelength or at a given band of wavelengths. As a result, the photoelectric sensor delivers a signal representative of the intensity of the optical response at that wavelength or in that band of wavelengths. Filtering the optical response of the reaction solution is an essential step in the methods implemented in prior art machines since it makes it possible to distinguish the fraction of the response that is associated with the optical agent (specifically a fluorescent agent) and that serves to quantify the presence of the agent, from a potential fraction of the optical response that might merely be transmission of the excitation radiation and/or that might come from interfering sources of optical radiation.

Prior art machines and methods are very satisfactory on numerous points. Nevertheless, a need has arisen to be able to further improve the measurement accuracy of such machines, in order to refine their results. In parallel, a need has arisen to be able to further increase the capacity of such machines, i.e. their ability to deliver more numerous analysis results, including on a single sample, without nevertheless increasing significantly the overall size of the machines.

For this purpose, the invention proposes a machine for automatic in vitro detection and/or quantification of analytes, in particular of microbiological origin, contained in samples, the machine being of the type comprising:
a plurality of optical analysis zones, each for receiving a reaction solution obtained by reaction with et sample; and an optical reader device capable of detecting and/or quantifying the optical response of the reaction solution to electromagnetic stimulation, the optical reader device comprising both at least one source of electromagnetic radiation capable of illuminating an analysis zone, and also a photoelectric receiver arranged to receive light radiation coming from the reaction solution contained in the analysis zone and capable of detecting the optical response of the reaction solution.

The photoelectric receiver is carried by a movable carriage of the machine that is motor-driven and that is moved under automatic control to bring the photoelectric receiver into a plurality of positions, each corresponding to a respective analysis zone.

According to the invention, the photoelectric receiver forms part of a k spectrometer capable of delivering a chromatic spectral decomposition of the optical response.

Other characteristics of the invention, that are optional, taken individually or in combination are as follows:

- the spectrometer is capable of delivering a chromatic spectral decomposition of the optical response over at least one working range of wavelengths between two wavelengths $\lambda_{min}$ and $\lambda_{max}$, with $\lambda_{max} \geq 2 \times \lambda_{min}$;
- the spectrometer includes a chromatic dispersion element and a main photoelectric sensor that is linear or two-dimensional;
- the spectrometer includes an electronic circuit that is connected to the photoelectric receiver and that delivers an image electrical signal that is an image of the chromatic spectral decomposition of the optical response;
- the image electric signal is an analog signal;
- the source of radiation is a monochromatic source;
- the source of radiation is a polychromatic source;
- the optical reader device includes means for detecting the intensity of the radiation emitted by the source of radiation;
- the means for detecting the intensity of the radiation emitted by the source of radiation include the spectrometer and a guide system for guiding a fraction of the incident radiation to the spectrometer without passing via the analysis zone; and
- the means for detecting the intensity of the radiation emitted by the radiation source include a secondary photoelectric sensor, distinct from the spectrometer, and a guide system for guiding a fraction of the incident radiation to the secondary photoelectric sensor without passing via the analysis zone.

The invention also provides a method of automatic in vitro detection and/or quantification of analytes, in particular of microbiological origin, contained in samples, the method being of the type comprising the following steps:

putting the sample in a situation to react with one or more reagents in order to produce directly or indirectly a reaction solution that, when a determined analyte is present in the sample, includes an optical agent having at least one predetermined optical property;

illuminating the reaction solution with electromagnetic radiation;

detecting the optical response of the reaction solution; and from the optical response, deducing the presence of and/or quantifying the analyte;

the method being characterized in that it implements one or more reagents for producing directly or indirectly a reaction solution including at least two distinct optical agents, each having at least one predetermined optical property, the two predetermined optical properties being distinct, and in that it includes the steps consisting in acquiring a chromatic spectral decomposition of the optical response and of separately detecting the two distinct predetermined optical properties in said spectral decomposition.

The invention also provides a method of automatic in vitro detection and/or quantification of analytes, in particular of microbiological origin, contained in samples, the method being of the type comprising the following steps:

putting the sample in a situation to react with one or more reagents in order to produce directly or indirectly a reaction solution that, when a determined analyte is present in the sample, includes an optical agent having at least one predetermined optical property;

illuminating the reaction solution with electromagnetic radiation;

detecting the optical response of the reaction solution; and from the optical response, deducing the presence of and/or quantifying the analyte;

the method being characterized in that it comprises the steps consisting in:

acquiring a chromatic spectral decomposition of the optical response;

determining an approximate theoretical relationship for variation of the intensity as a function of wavelength, which relationship is an image of the chromatic spectral decomposition of the optical response;

in the approximate theoretical relationship for variation of the intensity as a function of wavelength, determining a linear offset of intensity that is a linear function of wavelength; and determining a corrected theoretical relationship for the variation of the intensity as a function of wavelength, by correcting the approximate theoretical relationship as a function of the linear offset.

Other characteristics of the invention, that are optional, taken individually or in combination are as follows:

- the step consisting in determining an approximate theoretical relationship for the variation of the intensity as a function of wavelength comprises the step of fitting a curve to at least a portion of the chromatic spectral decomposition of the optical response;
- the step consisting in acquiring a chromatic spectral decomposition of the optical response comprises a step of chromatically dispersing a light beam coming from the optical response and of detecting the intensities of components at distinct wavelengths of the beam as dispersed in this way;
- the method includes a step of detecting the intensity of the radiation emitted by the source of radiation;
- the method includes a step of guiding a fraction of the incident radiation without passing via the analysis zone, and a step consisting in acquiring a chromatic spectral decomposition of said fraction of the incident radiation; and
- prior to the step consisting in acquiring a chromatic spectral decomposition of the incident radiation, a step of mixing said fraction of the incident radiation and the optical response of the reaction solution.

Various other characteristics appear from the following description made with reference to the accompanying drawings which show embodiments of the subject matter of the invention as non-limiting examples.

FIG. 4 shows a first embodiment of the invention including an optical reader device suitable for being mounted on a movable carriage and including a spectrometer.

FIG. 5 is a view similar to the view of FIG. 4, showing a second embodiment of the invention.

FIG. 1 shows a machine for automatic detection and/or quantification in vitro of analytes contained in samples.

More precisely, the automatic machine shown serves not only to perform detection and/or quantification steps, but also one or more steps of preparing a reaction solution from a sample.

The presently-described machine corresponds in particular to a machine of the type sold by the Applicant under the trade name "Vidas® 3". This type of machine makes it possible to perform biological analyses on biological samples in automatic manner, and to do so with it being possible on a single machine to perform different analyses on a single sample or on different samples.

Figure 1:
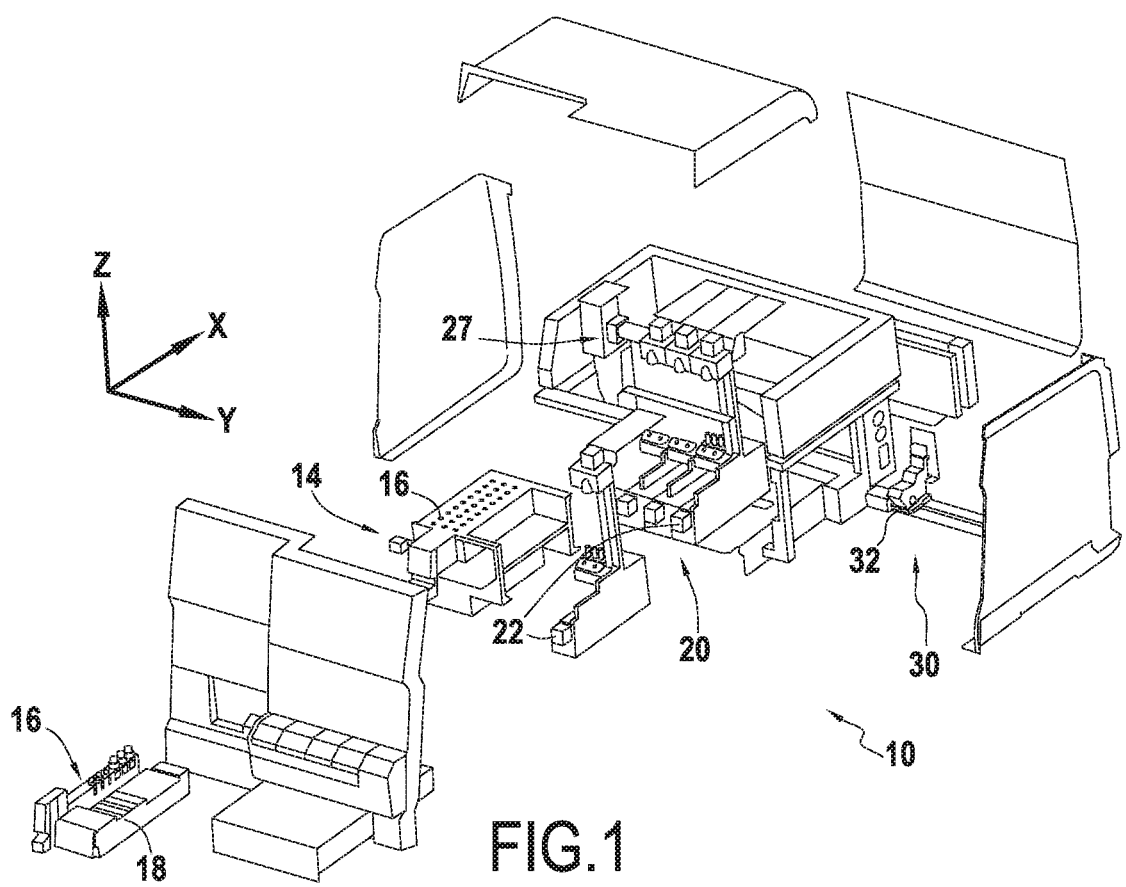
FIG. 1 is a diagrammatic perspective view of a machine for in vitro detection and/or quantification by optical analysis, in particular by fluorimetry and/or colorimetry, in which the invention may be incorporated, said machine incorporating a plurality of strips, each having an analysis zone.

A machine 10 of this type is shown diagrammatically in an exploded perspective view in FIG. 1. In a bottom left portion, referred to as the "pre-analytic" portion 14 of the machine, there can be a series of three primary drawers 16 and a secondary drawer 18 that are arranged side by side. Each of these drawers 16, 18 is designed to be movable independently of the others between a loading position and a utilization position, and specifically moving by linear sliding along a horizontal path that is perpendicular to a front face of the machine, in a direction X that is referred to as longitudinal. The terms "front", "rear", "horizontal", "vertical", etc. are used herein by way of indication with reference to the normal orientation of such a machine, as shown in the figures. By way of example, the primary drawers 16 are designed to receive samples, diluant substances, reagents, reference substances, etc. . . . , e.g. contained in containers of various shapes. Each primary drawer 16 may thus carry a plurality of containers, each container preferably being received in a predetermined location of the primary drawer 16. Each of the primary drawers 16 may be removable from the machine in order to enable drawers to be prepared and loaded away from the machine, thus making it possible to perform the preparation step while the machine is operating on other primary drawers in the utilization position. At its front end, each primary drawer 16 may include a grip handle. In this application example, the secondary drawer 18 is intended by way of example for receiving analysis tools, e.g. disposable tools used by the machine in the automatic analysis process. These tools, e.g. pipette endpieces or dilution cups, may be carried by removable trays that may be placed, preferably in predetermined locations, on the secondary drawer 18. The secondary drawer 18 may also be removable so that a plurality of secondary drawers 18 can be used in alternation on the machine.

Figure 2:
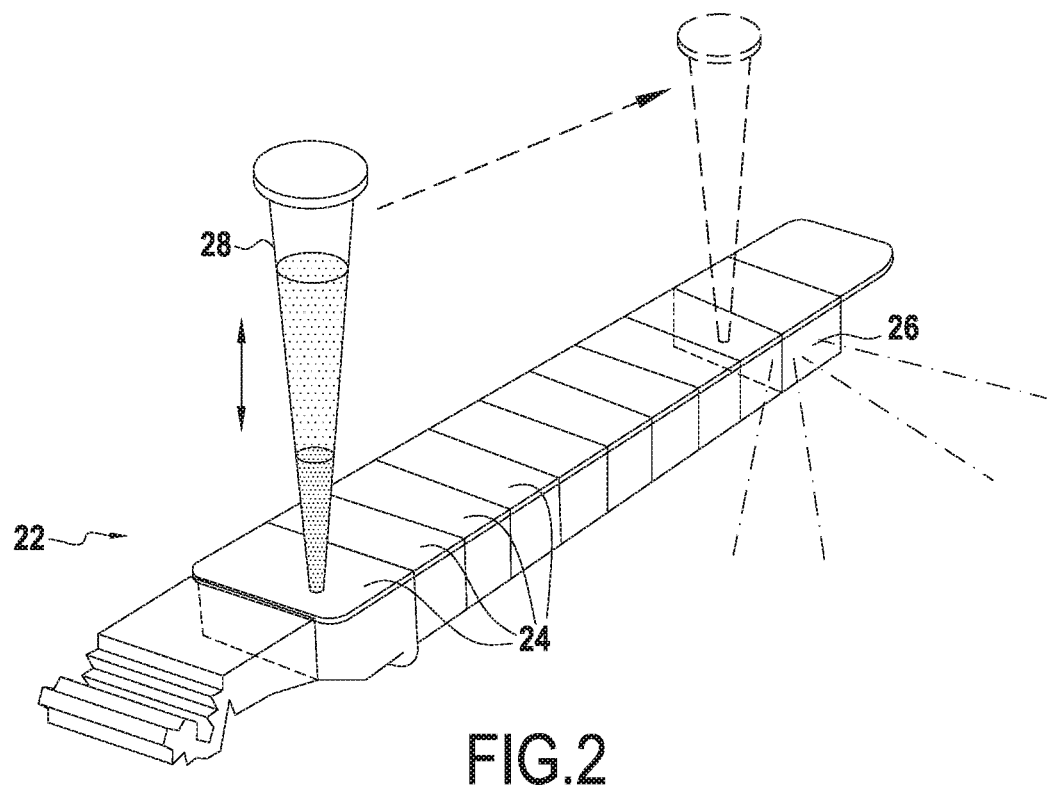
FIG. 2 is a view showing a strip including an analysis zone.

Furthermore, FIG. 1 shows a right-hand portion of the machine, sometimes referred to as the analytic portion 20, and that likewise includes locations that may for example receive analysis strips, which may be disposable, such as the strips shown in FIG. 2. The analysis strip 22 is a part that is generally made out of plastics material, in particular when it is disposable, as in this example. The strip 22 comprises a main body defining a series of containers 24 that are upwardly open. The strip is elongate in a longitudinal direction such that the containers 24 are in alignment as a single row in the longitudinal direction, which is to correspond to the front/rear direction of the machine 10. Prior to using the strip 22, at least some of the containers 24, and preferably all of the containers, are closed by a leaktight film that covers the top face of the strip 22 hermetically, such that the containers 24 are isolated from one another. Before the strips are used, the containers 24 are either empty, or else filled with a substance that may for example comprise a buffer solution, a washing solution, a diluant, a reagent, etc. . . . Nevertheless, in the example shown, when the strip is in place in the machine in a utilization position, the last container or rear container 26 of the strip is designed to coincide geographically with an optical analysis zone 26' of the machine.

In the example shown, a strip is adapted to one or more types of analysis by the nature of the substances that are provided in the various containers, with it not being essential for all of them to be in use in any given analysis.

In the machine shown, the machine 10 is designed to receive a plurality of analysis strips 22 simultaneously. These strips 22 are designed to be arranged parallel to one another, side by side, the strips thus being in alignment in a transverse direction Y that is perpendicular to their longitudinal direction X. In the example shown, the machine 10 is thus designed to be capable of receiving 12 analysis strips 22 side by side in the analysis position. In this position, the rear container 26 of each strip 22 coincides with a corresponding optical analysis zone 26' of the machine. In other words, the machine has a plurality of analysis zones 26', and in a machine using analysis strips such as the strips 22, each analysis zone 26' of the machine is designed to receive the rear container 26 of a strip. Insofar as the rear container 26 contains a final reaction solution, this final reaction solution is collected in the corresponding analysis zone 26'.

There follows a succinct description of the operation of the machine 10 shown. An operator loads one or more samples for analysis in the containers of the primary drawers 16. The operator may also load these containers with substances needed for preparing the sample and/or for preparing reactions. The operator also loads into the secondary drawer 16 the items needed for this preparation.

In the example shown, the machine 10 includes automatic preparation and k reaction means that prepare the sample and cause it to react with reagents in order to provide a final reaction solution that presents an optical response to excitation by electromagnetic radiation suitable for enabling analysis results to be deduced.

For this purpose, the machine 10 includes a movable pipetting device 27 that is preferably movable in all three directions: longitudinal X (front/rear), transverse Y (left/right) and vertical Z (up/down). The movable pipetting device 27 is capable of taking an individual pipette endpiece 28 (visible in FIG. 2) from the secondary drawer 18 and, with the help of this individual pipette endpiece 28, of taking or depositing substances (samples, reagents, diluants, buffer solutions, etc. . . . ). The substances may be taken from the containers of the primary drawers or from containers of an analysis strip. The substances and samples that are taken may be mixed together, either in an individual pipette endpiece, or else in dilution cups present in the secondary drawer 18, or indeed in one of the containers of one of the analysis strips 22. During these various steps, the analyte present in the samples is caused to react with the substances, in particular the reagents, with which it is put into contact. Among the substances used there is a precursor of an optical agent, which optical agent has at least one predetermined optical property (color, fluorescence, phosphorescence, . . . ).

As a function of the presence of the looked-for analyte, and possibly as a function of its concentration, the precursor will cause a quantity of the optical agent to be formed in a final reaction solution. The final reaction solution thus possesses an optical agent, e.g. a fluorescent agent, at a concentration that is representative of the presence of the looked-for analyte in the initial sample. In known manner, it is thus sought to determine the optical response of the final reaction solution and in particular to detect the predetermined optical property of the optical agent in order to deduce an analysis result therefrom.

Preferably, the optical agent is present in the reaction solution or possesses the predetermined optical property only in the presence of the determined analyte. Preferably, the intensity of the predetermined optical property is a function of the quantity or concentration of the analyte in the determined sample. Advantageously, this predetermined optical property can be detected by analyzing a chromatic spectral decomposition of radiation emitted by the reaction solution when the solution is subjected to incident electromagnetic radiation.

By way of example, the optical agent is a fluorescent agent and the predetermined optical property is fluorescent emission, which may for example be characterized by a particular chromatic spectral decomposition when the reaction solution is illuminated by an appropriate excitation electromagnetic radiation.

The optical agent could equally well be a colored agent, in which case the predetermined optical property is color, which may be determined by a chromatic absorption spectrum when the reaction solution is illuminated by appropriate incident electromagnetic radiation. Nevertheless, under such circumstances, it can be seen that the system needs to operate in transmission with the source of electromagnetic radiation (or a reflection of it) being in alignment with the receiver.

For this purpose, it is known to arrange a certain quantity of the final reaction solution in an optical analysis zone 26' that coincides, in the example shown, with the rear container 26 of the analysis strip 22 when the strip is in the utilization position. It is also known, in particular from the above-mentioned Vidas® 3 machine, that it is possible to use an optical reader device 30 that includes both at least one source of electromagnetic radiation capable of illuminating the analysis zone, and also a photoelectric receiver arranged to collect light radiation coming from the reaction solution contained in the analysis zone. The reader device can thus detect the optical response of the final reaction solution, and as a function of this optical reading, it becomes possible to determine the presence, and possibly the concentration, of the optical agent that is specific to the analysis.

It can thus be understood from the above-described operation that the machine 10 is capable of having a plurality of analysis strips 22 engaged simultaneously in the machine 10 and is thus capable of performing in parallel a corresponding quantity of different analyses, each being suitable for producing a final reaction solution for which it must be possible to detect the optical response. It should be observed that two distinct analysis strips may be used and engaged in parallel in the machine in order to perform two distinct analyses on a single sample, in order to perform the same analysis on different samples loaded into a primary drawer 16, in order to perform the same analysis on two portions of a single sample, e.g. for redundancy purposes, etc. . . . Under such circumstances, the two rear containers 26 of the two strips are designed to coincide with a corresponding number of optical analysis zones 26', each considered as containing a final reaction solution for analysis.

For this purpose, the optical reader device 30 is mounted on a movable carriage 32. The movable carriage 32 is motor-driven and its movements are controlled automatically by the machine 10 in order to bring the reader device 30 into various positions. At least some of these positions correspond to respective analysis zones. In the example shown, the movable carriage 32 is movable in one direction only, specifically the transverse direction Y of the machine 10, in order to be brought into positions along the transverse direction that correspond to the k transverse positions of the various analysis zones 26' coinciding with the rear containers of analysis strips 22 potentially engaged in the machine 10. The movable carriage 32 is preferably capable of being taken to as many different positions as there are different analysis zones 26' in the machine.

Figure 3:
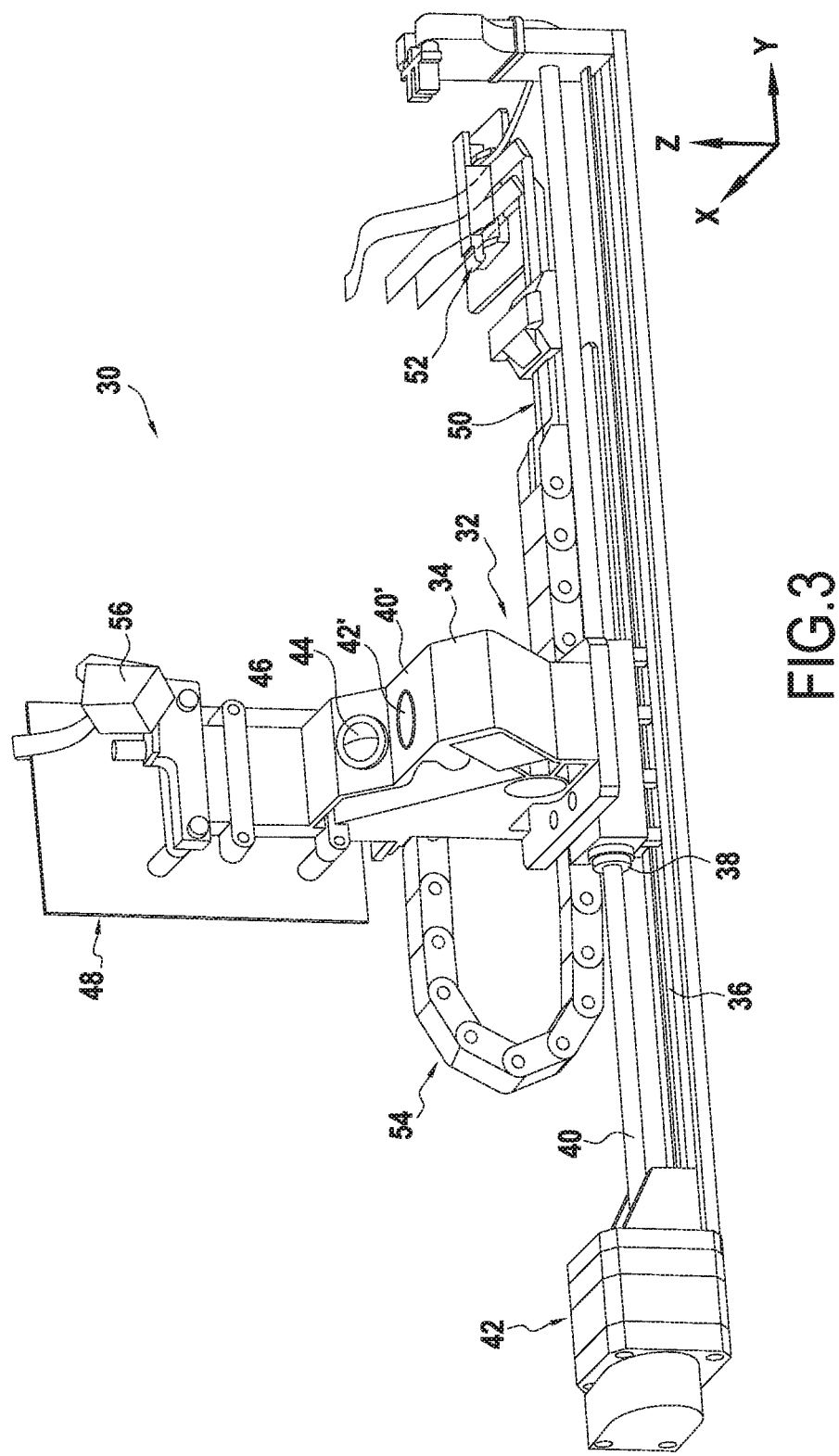
FIG. 3 is a diagrammatic perspective view showing an embodiment of a movable carriage carrying an optical reader device for reading the optical response of a reaction solution contained in an analysis zone.

FIG. 3 shows one possible embodiment of the control means that serve to move the movable carriage 32. The movable carriage 32 comprises a body 34 with a bottom end that co-operates with a slideway 36 for guiding the movable carriage 32 along the transverse direction Y. Furthermore, the bottom end of the body 34 is provided with a nut system 38 that co-operates with a drive screw 40 extending along a transverse axis. The drive screw 40 is driven in rotation by an electric motor 42. It can thus be understood that appropriately driving the electric motor 42 in one direction of rotation or the other will act via the screw-and-nut system formed by the drive screw 40 and the nut 38 connected to the body 32 to cause the body 32 to move along the transverse direction one way or the other. Furthermore, a system for detecting the position of the carriage, which may rely for example on information delivered by a rotary encoder associated with the motor 42 or on information delivered by sensors arranged along the path of the movable carriage 32, may advantageously be provided to give the position of the movable carriage 32 along the slideway 36. The slideway 36 is stationary relative to the machine, and the motor 42 and the screw 40 are likewise stationary relative to the machine, ignoring their own movements in rotation. Thus, the electric motor 42 controls the movement of the carriage 32. The electric motor 42 is itself controlled by a central control unit of the machine 10. Naturally, other means for moving the movable carriage could be provided. Likewise, the movable carriage could move along a linear path as in this embodiment, or along a curved path, or indeed it could be capable of being moved in two directions in a plane, or even in three directions in three-dimensional space. Likewise, the control means that serve to move the carriage could be other actuators and/or other mechanisms for transforming the movement of an actuator into a movement of the carriage.

In the embodiment shown, the body 34 of the movable carriage includes a working zone having two surfaces that are inclined relative to each other, both extending in a transverse direction. A first working surface 40, which is horizontal in this embodiment, is provided with a first window 42. A second working surface 44 containing the transverse direction but sloping relative to the longitudinal direction presents a second window 46. These two working surfaces are for bringing face to face with an analysis zone 26' so that the reader device can emit excitation k electromagnetic radiation through one of the windows, e.g. light radiation in the visible, ultraviolet, or infrared range, towards the analysis zone 26', and can receive the optical response of the analysis zone 26' through the other window.

In the example shown in the figures, it can thus be understood that the carriage 32 carries both a source of excitation electromagnetic radiation and a photoelectric receiver. Nevertheless, in a variant, provision could be made for only the photoelectric receiver to be on board the movable carriage 32, with the source of excitation electromagnetic radiation being stationary in the machine, for example. It can also be seen that in the embodiment shown the carriage 32 includes an electronic card 48 serving in particular to perform at least part of the driving and the signal processing of the source of electromagnetic radiation and of the photoelectric receiver. This electronic card 48 moves with the carriage 32 and the electric signals useful for the card 48 are transmitted to a central control unit of the machine by a wire harness 50 that preferably includes at least one portion that is flexible and thus deformable in reversible manner in order to allow the carriage to move. By way of example, the harness 50 is connected to a stationary terminal block of the machine 10. In the example shown, it is received in a roll-up guide 54 made up of hinged links for guiding deformation during movements of the carriage, thus preventing the harness from interfering in the mechanism for moving the carriage. It should also be observed that the movable carriage 32 can include other devices, e.g. such as an optical bar code reader 56. Preferably, the electronic card 48 outputs digital electric signals. Thus, electric signals that are transmitted through the wire harness 50 in digital form are much less sensitive than analog signals would be to the disturbances that might be generated around the harness.

A first embodiment of a reader device of the invention, on board a movable carriage 32, is shown in FIG. 4. In this section view on a plane perpendicular to the transverse travel direction of the movable carriage, there can be seen firstly, fastened to the body 34, a source 58 of electromagnetic radiation for exciting the optical agent present in the final reaction solution contained in the analysis zone 26'. FIG. 4 also shows the presence of a rear container 26 of a strip 22 coinciding with an analysis zone 26' in a working position relative to the reader device 30, enabling it both to excite the optical agent and to detect its optical response.

FIG. 4 shows that the reader device 30 has a source of electromagnetic radiation, which is fastened to the body 34 of the movable carriage 32 below the first working surface 42, in this embodiment. It may advantageously be oriented so as to emit excitation electromagnetic radiation towards the analysis zone 26' through the first window 42. Nevertheless, an optical guide device such as an optical fiber or one or more mirrors, one or more prisms, etc. . . . could be used for guiding radiation from the source 58 to the first window 42, in which case the source 58 may be arranged in some other way on the movable carriage, e.g. by being mounted on the electronic card 48. The source of electromagnetic radiation may be a source of radiation in the optical range, i.e. radiation having a wavelength in the range 10 nanometers (nm) to 1 millimeter (mm), including in particular ultraviolet radiation, visible light, and infrared radiation. In the example shown, the source 58 is a monochromatic source. Nevertheless, in a variant, it is possible to envisage a polychromatic source, having a chromatic spectrum that is discrete, or continuous, or a combination of both. Likewise, the source 58 may be constituted by a single component, e.g. an incandescent filament, a light-emitting diode, a laser diode, or a fluorescent tube, or it may be made up of a plurality of components in combination, whether of the same type or of different types. The radiation from the source 58 may optionally be conditioned by a conditioning system that may comprise, as shown in FIG. 4: a chromatic filter 60 (e.g. highpass, lowpass, bandpass, and/or polarizing, etc. . . . ); a diaphragm (not shown); and one or more lenses 62. For example, a filter 60 that passes wavelengths suitable for excitation serves to limit the presence of other wavelengths that might disturb the measurement. The conditioning system is preferably carried by the body 34 and arranged between the source 58 and the first window 42. In the example shown, a beam separator is provided at the window 42, e.g. in the form of a plate having parallel faces 63 that are partially reflecting, or a semi-reflecting prism, serving to take a fraction of the radiation emitted by the source 58 for a purpose that is described below. In the example shown, the beam separator 63 thus comprises a semi-reflecting plate with parallel faces, which separator is arranged at the window 42 between the source 58 and the analysis zone 26'. It extends in a plane that forms an angle of 45° relative to a main direction I of incidence of the electromagnetic radiation emitted by the source 58. As shown in FIGS. 4 and 5, the incident radiation emitted by the source 58 illuminates the analysis zone 26'. In the example shown, it can be seen that the analysis zone 26', which coincides with the rear container 26 of an analysis strip in the example shown, presents at least one inlet window for admitting incident radiation, and that is made of a material that is transparent to the radiation from the source 58. In the present example, this window is constituted by a face of a side wall of the rear container 26 that extends substantially perpendicularly to a main direction I of incidence of the electromagnetic radiation emitted by the source 58. Thus the final reaction solution contained in the analysis zone is illuminated by the radiation emitted by the source 58.

In the example shown, the shortest light path between the source 58 of excitation electromagnetic radiation and the analysis zone 26' extends in a straight line in the sense that the optical system for conditioning the excitation radiation emitted by the source 58 does not give rise to a change in direction of the optical axis between these two elements. This shortest light path thus defines a main incident direction I for the excitation electromagnetic radiation emitted by the source 58 towards the analysis zone 26'. In the example shown, it can be seen that this main incident direction I slopes relative to the first working face 40 of the body 34 at an angle that may lie in the range 30° to 60°, e.g. 45°, these values merely being illustrative of the embodiment. This main incident direction I is substantially parallel to the second working surface 44 of the body. In the example, the partially reflective blade 63 presents a semi-reflecting plane surface that is oriented at an angle, e.g. at 45°, relative to the main incident direction I in order to enable a fraction of the intensity of the beam, 50% or less, to be reflected via a reference channel, as described below, while allowing the other fraction of the intensity of the beam to go to the analysis zone 26'.

In an aspect of the invention, the movable carriage 32 includes a photoelectric receiver that forms a portion of a spectrometer 64 in the embodiment shown.

The spectrometer used in the embodiment shown is an optoelectronic component capable of delivering an electronic signal that is representative of the chromatic spectral decomposition of radiation received by the spectrometer. For electromagnetic radiation in the range of the optical system, and in particular in the visible range, the infrared range, and/or the ultraviolet range, where the radiation is considered as being a superposition of individual monochromatic waves, this decomposition represents the distribution of the intensity of each individual wave as a function of the wavelength of the individual wave.

Because the spectrometer 64 is installed on the movable carriage 32, the radiation received by the spectrometer can normally include the optical response of the final reaction solution contained in an analysis zone 26', whenever that zone is illuminated by the excitation electromagnetic radiation emitted by the source 58.

In the example shown, the spectrometer 64 essentially comprises an inlet diaphragm 66, a chromatic dispersion element 68, and a photoelectric sensor 70.

The spectrometer 64 presents a field of view corresponding to the portion of three-dimensional space seen by the photoelectric sensor 70 through the chromatic dispersion element 68 and the inlet diaphragm 66.

In the embodiment shown, the spectrometer 64 is arranged on the body 34 so that for a determined position of the movable carriage 32, its field of view through an optical conditioning system of the receiver covers the corresponding analysis zone 26' in such a manner that light radiation emitted by a final reaction solution contained in the analysis zone 26' is directed by the optical conditioning system of the receiver to the inlet diaphragm 66 of the spectrometer in an appropriate direction. The optical conditioning system of the receiver may be carried by the body 34 and may be arranged between the spectrometer and the second window 46. The optical conditioning system of the receiver may optionally include in particular a chromatic filter (not present in the embodiment of FIG. 4, but that might for example be a highpass filter, a lowpass filter, a bandpass filter, and/or a polarizing filter, etc. . . . ), a diaphragm (not shown), and/or one or more lenses 74. An optical guide device such as an optical fiber, one or more mirrors, one or more prisms, a light guide of frustoconical shape as shown in FIG. 4, etc., may be used to guide radiation from the second window 46 to the spectrometer 64, preferably via the inlet diaphragm 66 in a predefined inlet direction. For example, the optical conditioning system of the receiver may be designed to deliver a collimated beam of radiation coming from the analysis zone 26' to the inlet of the spectrometer.

The inlet diaphragm 66 may be a substantially circular spot diaphragm perpendicular to the predefined inlet direction of the spectrometer 64, or preferably it is a linear diaphragm made in the form of a slot.

The photoelectric sensor 70 may be a linear sensor or a two-dimensional sensor. It may be a sensor making use of technology of charge-coupled device (CCD), or complementary metal oxide on silicon (CMOS), or other type.

The chromatic dispersion element 68 gives rise to chromatic dispersion of the incident beam, in the sense that on interacting with the chromatic dispersion element a polychromatic incident beam, e.g. a parallel beam, has its various chromatic components deflected from their path by an angle that depends on the wavelength of the chromatic component under consideration. A chromatic dispersion element 68 may comprise a diffraction grating. A diffraction grating may in particular comprise a series of parallel slots (transmission grating) or of reflecting rulings (reflection grating). These slots or rulings are spaced apart regularly, with the spacing being refereed to as the "pitch" of the grating. A chromatic dispersion element 68 could also be embodied in the form of one or more refractive surfaces, e.g. by using a refractive prism, in which the chromatic dispersion is obtained by refraction, or indeed in the form of a combination of one or more refractive surfaces together with one or more diffraction gratings. In the embodiment shown, the diffraction grating is represented as forming part of a concave reflective surface that returns the dispersed radiation towards the photoelectric sensor, thereby enabling the spectrometer to be very compact.

In the embodiment shown, the shortest light path between the analysis zone 26' and the inlet diaphragm 68 of the spectrometer 64 extends along a straight line in the sense that the optical system for conditioning the optical response does not give rise to a change of direction in the optical axis. This shortest light path thus defines a main return direction R for the optical response from the analysis zone 26' to the spectrometer 64. In the embodiment shown, it can be seen that this main return direction R is perpendicular to the second working surface 44 of the body. It may be observed that the main direction I of incidence going from the source 58 towards the analysis zone 26', and the main return direction R going from the analysis zone 26' towards the spectrometer 64 are preferably not simultaneously parallel and in the same direction, in particular for analysis by fluorimetry for fluorescent optical agent detection. On the contrary, they form between them some minimum angle, e.g. at least 45°, with the convention that directions that are parallel, but opposite, form between them an angle of 180°. In the embodiment shown, the main direction I of incidence and the main return direction R are perpendicular, thus serving to limit any risk of interference in the optical response from the incident radiation. In a variant, the main direction I of incidence going from the source 58 towards the analysis zone 26', and the main return direction R going from the analysis zone 26' towards the spectrometer 64, may be parallel or almost parallel, but in opposite directions, with the source 58 and the spectrometer being arranged on the same side of the analysis zone 26'. Preferably, the rear container 26 presents an outlet window for the optical response that extends substantially perpendicularly to the main return direction R.

When performing analysis by transmission, in particular for colorimetric analysis by detecting an optical agent of the chromatic type, the main direction I of incidence and the main return direction R are preferably aligned with the inlet and the outlet of the analysis zone 26' and thus with the main direction I of incidence going from the source 58 towards the analysis zone 26', and the main return direction R going from the analysis zone 26' towards the spectrometer 64, which directions are parallel and in the same direction, unless a reflector is used to deflect one of the two beams.

Advantageously, the dispersion element 68 and the photoelectric sensor 70 are arranged inside a housing 76 having the inlet diaphragm 66 formed therein.

Naturally, for reasons of ensuring the device is compact, it is appropriate to use a spectrometer 64 of small dimensions. Various versions of spectrometers suitable for use in the context of the invention are proposed by way of example by the Japanese supplier Hamamatsu Photonics KK, 325-6, Sunayama-cho, Naka-ku, Hamamatsu City, Shizuoka Pref., 430-8587, Japan. For example, in the context of the invention, it is possible to use one of the spectrometers in the "Mini-spectrometer" range, such as the reference C10988M1-01, or in the "Micro-spectrometer" range, such as the reference C12666MA, or the reference C12880MA.

In the example shown, the housing 76 is a rectangular box-shaped housing having a front wall 78 facing towards the second window 46 and oriented substantially perpendicularly to a main inlet direction of radiation into the spectrometer. Specifically, the front wall 78 is provided, substantially in its center, with the inlet diaphragm 66, which in this embodiment is in the form of a slot. Inside the housing 76, a concave reflective surface carrying the diffraction grating 68 returns an incident beam in the form of a chromatic dispersion towards the photoelectric sensor 70, which is arranged against the inside face of the front wall 78. The photoelectric sensor 70 is thus laterally offset relative to the inlet slot 66, and its sensitive surface faces towards the rear of the housing 76, facing the reflective surface carrying the diffraction grating 68. Such a construction has the advantage of being very compact, thus enabling such a spectrometer to be contained in a housing 76 having a volume that may be less than 10 cubic centimeters ($cm^3$).

The spectrometer 64 delivers an electronic signal representative of the chromatic spectrum decomposition of the radiation entering through the inlet diaphragm 66. This electronic signal is produced by an electronic circuit associated with the photoelectric sensor 70. The electronic circuit may be incorporated in the housing 76, adjacent thereto, or it may be carried at least in part by the electronic card 48 that is associated with the movable carriage 34. The electronic signal may comprise an analog signal, but it preferably comprises a digital signal, since that is less sensitive to disturbance. The signal may be completely digital. It is advantageously transmitted to the central control unit of the machine via the wire harness 50.

The spectrometer is preferably capable of delivering a chromatic spectral decomposition of the optical response over at least one working range of wavelengths extending from a first wavelength to a second wavelength that is twice the first. For example, a working range of wavelengths may extend between two wavelengths $\lambda_{min}$ and $\lambda_{max}$, with $\lambda_{max} \geq 2 \times \lambda_{min}$. Specifically, the use of a spectrometer on board the movable carriage 34 makes it possible to obtain information about the spectral composition of the optical response. Analyzing this information over a certain meaningful range makes it possible, as described below, to refine the results of the analysis. Naturally, the working range of the spectrometer is selected to correspond to the particular optical properties of the optical agent that is to be detected in the final reaction solution. Advantageously, the working range of the spectrometer 64 is such as to enable it to cover two distinct predetermined optical properties, in particular two distinct wavelengths, each corresponding to at least two distinct optical agents, or indeed more than two distinct optical agents.

It can be understood that a machine as described above is advantageously used when the reaction solution includes at least one fluorescent agent for which the presence and/or the quantity in the reaction solution depend on the presence and/or the quantity of a looked-for analyte in the sample. Naturally, care is taken to ensure that the emission spectrum of the fluorescent agent is included at least in part in the working range of wavelengths of the spectrometer.

The excitation electromagnetic radiation emitted by the radiation source 58 preferably presents a spectrum that is distinct from the emission spectrum of the looked-for optical agent. Still more particularly, the two spectra are disjoint in the sense that each of them is contained in a range of wavelengths and the two ranges of wavelengths do not overlap. This makes it possible in particular to further limit any risk of the optical response being interfered with by the excitation radiation.

The optical reader device may also include means for detecting the intensity of the radiation emitted by the source of radiation.

These means may comprise a circuit or an algorithm for estimating the intensity emitted by the source 58, e.g. as a function of control parameters of the source 58 and of known characteristics of the source. For example, the electronic card 48 may include a computer memory storing instructions for implementing the algorithm and a microprocessor unit for executing said instructions in order to determine the light intensity as a function of control parameters, with the intensity as determined being transmitted to the central control unit via the harness 50. In a variant, the control parameters and the instructions are stored in a computer memory of the central unit, of the computer type, which executes said instructions in order to determine the light intensity.

Nevertheless, these means may comprise a photoelectric detector measuring the actual intensity of the excitation radiation emitted by the source 58.

In the embodiment shown in FIG. 4, the means for detecting the intensity of the radiation emitted by the source 58 of excitation radiation include a secondary photoelectric sensor 80 that is distinct from the spectrometer 64. The secondary photoelectric sensor 80 may be a photodiode, for example. The secondary photoelectric sensor 80 is sensitive to the wavelength or to the range of wavelengths emitted by the source 58.

Advantageously, the optical reader device includes a guide system for guiding the excitation radiation, which system guides a fraction of the incident radiation to the secondary photoelectric sensor, without passing through the analysis zone. In the embodiment of FIG. 4, this guide system includes for example a beam separator, e.g. in the form of a semireflecting plate 63 having parallel faces, which directs a fraction of the radiation emitted by the source 58 to the secondary sensor 80. This fraction of the emitted radiation, which is separated by the beam separator 63, is referred to as being the reference beam. The guide system may include a filter 82 and/or for example: one or more lenses, or indeed one or more elements including optical fibers, prisms, mirrors and/or a light guide of frustoconical shape, as shown in FIG. 4 downstream from the filter 82, for the purpose of conveying the reference beam to the secondary sensor 80. The reference beam does not pass through the analysis zone 26' on its path between the source 58 and the secondary sensor 80. As a result, the secondary sensor 80 is capable of delivering information, e.g. in the form of a reference electric signal, that is an image of the intensity of the radiation emitted by the source 58.

FIG. 5 shows a second embodiment of the invention, which is identical to the first embodiment shown in FIG. 4 in all points, except concerning the means for detecting the intensity of the radiation emitted by the source 58 and the possible presence of a filter 72 on the path of the optical response. Unlike the embodiment shown in FIG. 4, these means for detecting the intensity of the radiation emitted by the source 58 do not rely on a secondary sensor distinct from the spectrometer 64, but make use of the spectrometer 64 for detecting the intensity of the radiation emitted by the source 58. In similar manner to the embodiment of FIG. 4, the detector means comprise a guide system for guiding the reference beam that is separated by the beam separator 64, The guide system may comprise elements that are identical or similar to those mentioned above for the guide system in the above embodiment. In contrast, the guide system conveys the reference beam to the inlet diaphragm 66 of the spectrometer 64. This embodiment is advantageous in that it does not require a distinct optoelectronic component for detecting the intensity of the electromagnetic signal emitted by the source 58. In this second embodiment, it should be observed that the system for guiding the reference beam also ensures that the reference beam does not pass through the analysis zone 26'. Furthermore, in the example shown, the reference beam does not pass through a filter after being reflected by the beam separator 63.

This second embodiment is particularly advantageous when the emission spectrum of the source 58 is distinct, and preferably disjoint, relative to the optical property that is characteristic of the optical agent that it is desired to detect. Specifically, under such circumstances, the spectrum decomposition information supplied by the spectrometer 64 serves to identify very clearly and distinctly the intensity peak(s) corresponding to distinct wavelengths, both for the radiation emitted by the source 58 and also for the radiation corresponding to the optical response of the final reaction solution under analysis.

It should be observed that in this second embodiment, the reference beam may optionally be mixed with the optical response coming from the analysis zone prior to entering through the diaphragm 66 of the spectrometer 64.

Nevertheless, in a variant of this second embodiment, it would also be possible to make provision for conveying only one or the other of the reference beam and the optical response to the spectrometer 64 in alternation, with the other one being shut out. Under such circumstances, the spectrometer 64 determines in succession the intensity of the reference beam and then the chromatic spectrum decomposition of the optical response of the analysis zone 26'. This variant, which retains the advantage of a single photoelectric sensor, may be advantageous in the event of the spectrum of the excitation radiation emitted by the source 58 overlapping at least in part with the optical response spectrum from the analysis zone 26'.

In the embodiment of FIG. 5, it may be observed that it is possible, optionally, to provide an optical filter 72 on the path of the optical response. Preferably, such a filter passes the wavelength of the working range of the spectrometer, needed for detecting the looked-for optical agent. The absence of a filter on the path of the optical response nevertheless makes it possible to operate the system with other optical agents that emit at different wavelengths, without requiring physical adaptation. Likewise, the presence of a filter on the path of the reference beam is possible, but optional. The absence of such a filter, as shown in FIG. 5, makes it possible to operate the system with sources 58 of different wavelengths, without requiring physical adaptation of the system.

Below, there follows a description of an analysis method as made possible by using a machine of the invention in the context of an application in which the fluorescent optical agent emits radiation having a defined wavelength or a narrow range of wavelengths defined or presenting a spectral decomposition possessing one or more characteristic peaks in a defined wavelength range. Naturally, the spectrometer 64 possesses a working range covering this wavelength or this range of wavelengths corresponding to the fluorescent agent. Advantageously, the fluorescent agent is selected so that its fluorescence is triggered by excitation from radiation at a wavelength that is different from the fluorescence wavelength(s). For example, the invention may be used in the context of an application implementing a fluorescent agent that is commonly referred to as 4-MU (4-methylumbelliferone), which is suitable for being excited by radiation in the ultraviolet range, e.g. radiation having a wavelength of 370 nm (±5 mn), and that emits fluorescent radiation in a wavelength range having its peak situated at about 450 nm (with a radiation range that may extend from about 375 nm to 550 nm). Another example of a fluorescent agent is "QuantaBlue®" available from Thermo Fisher Scientific, Pierce Biotechnology, PO Box 117, Rockford, Ill. 61105, United States, which presents a fluorescence emission peak at 420 nm on being excited by excitation radiation at 325 nm. From the same supplier, it is possible by way of example to use the agents Qdot˘ 605, Qdot˘ 705, or Qdot˘ 525. Nevertheless, on each occasion, it is necessary to take care to ensure that the light source is adapted so that it does indeed emit appropriate excitation radiation.

Figure 6:
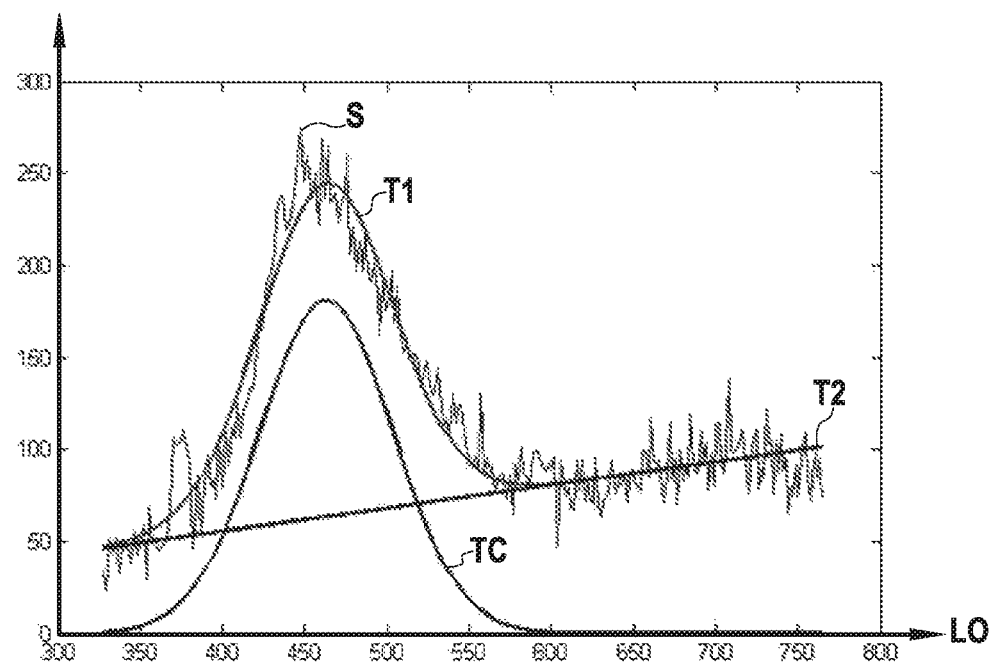
FIG. 6 shows a chromatic spectral decomposition obtained in the context of the invention.

FIG. 6 shows the chromatic spectral decomposition delivered by the spectrometer 64 when a solution containing a 4-MU fluorescent agent has been placed in an analysis zone 26', with the analysis zone being illuminated by the source 58 of excitation radiation that is constituted by this example by a light-emitting diode emitting in the ultraviolet range, and in particular in a narrow range of wavelengths of 370 nm±5 nm. In the graph of FIG. 6, the ordinate axis represents a magnitude that is an image of the intensity of a chromatic component of the radiation, which is plotted along the abscissa axis as a function of the wavelength LO of the chromatic component of the radiation received by the spectrometer 64.

The signal delivered by the spectrometer 64 is an irregular signal S. Nevertheless, this signal presents a general shape that clearly presents an intensity peak with a maximum that is reached around a wavelength of 450 nm. Nevertheless, it should be observed that on either side of the intensity peak that extends from 350 nm to 550 nm, the signal S is not zero. This non-zero portion of the signal represents disturbances or interfering elements that are not directly associated with the fluorescence of the fluorescent agent.

A second aspect of the invention thus consists in proposing a method of better isolating the characteristic of interest in the signal delivered by the spectrometer, which characteristic corresponds specifically to the optical property that is characteristic of the optical agent that is to be detected and/or quantified.

Thus, an aspect of the invention proposes a method for refining the results obtained by an analysis.

Such a method may be used for automatic in vitro detection and/or quantification of analytes contained in samples. It may advantageously be implemented by means of a machine of the invention. In particular, the data processing steps of the method are implemented by the central unit in charge of controlling the machine and comprising a computer having a computer memory storing all of the parameters and instructions needed for implementing said steps. The results of the method are stored in the central unit and/or displayed on a screen, with which the machine is provided, for example. In a variant, the central unit is connected to a remote computer to which it communicates the control and measurement parameters used by the machine for implementing said steps, and for storing and/or displaying the results thereof.

In such a method, it is possible to put a sample in a situation where it reacts with one or more reagents in order to produce directly or indirectly a reaction solution that includes, in the presence of a determined analyte in the sample, an agent having at least one predetermined optical property, e.g. a color, phosphorescence, or luminescence. Preferably, the optical agent is present in the reaction solution or possesses the predetermined optical property only in the presence of the determined analyte. Preferably, the intensity of the predetermined optical property is a function of the quantity or concentration of the analyte in the determined sample. Advantageously, this predetermined optical property is detectable by analyzing a chromatic spectral decomposition of radiation emitted by the reaction solution when the radiation is subjected to incident electromagnetic radiation. By way of example, the optical agent is a fluorescent agent and the predetermined optical property is then fluorescent emission, which may for example be characterized by a particular chromatic spectral decomposition.

This step may be performed in the machine as described above, in particular concerning the steps of processing data in its central unit or in a remote computer as described above, or it may be performed in some other machine, or manually, or by any other means.

Thereafter, the method makes provision for illuminating the reaction solution with excitation electromagnetic radiation. To do this, the reaction solution is placed in an analysis zone, e.g. coinciding with the rear container 26 of an analysis strip 22 as described above. The illumination may be performed by the source 58 of the above-described machine.

The method makes provision for detecting the optical response of the reaction solution and for deducing from the optical response the presence and/or the quantity of the analyte. Advantageously, the optical response is detected by the above-described machine, and in particular by interpreting the chromatic spectral decomposition of the optical response as obtained by the spectrometer 64.

In a step of the method, an approximate theoretical relationship is determined for variation of the intensity as a function of wavelength, that is an image of the chromatic spectral decomposition of the optical response.

This approximate theoretical relationship may be obtained graphically or mathematically. It is advantageously obtained by any known curve-fitting method. Curve-fitting methods may include fitting by the least squares methods.

FIG. 6 shows an example in which two portions are identified in the theoretical relationship. A portion T1 that corresponds well to the intensity peak extending from about 350 nm to about 550 nm. This portion T1 may be predefined as being a polynomial curve or a Gaussian curve or any other parametric curve, and it is then possible using known regression methods to determine the portion T1 of the theoretical relationship. A portion T2 of the theoretical relationship is a linear relationship that corresponds best to the signal S away from the intensity peak that extends from 350 nm to 550 nm. This portion T2 of the theoretical relationships may be determined by linear regression, for example.

In the approximate theoretical relationships for variation of the intensity as a function of wavelength, it is thus possible to determine a linear offset for the intensity, which is a linear function of wavelength, that affects the curve as a whole. In the example shown, this linear offset may be considered to be the linear portion T2 of the theoretical relationship. In reality, this linear offset may be associated by way of example at least in part with differential absorption of the radiation by the material constituting the rear container 26 of the analysis strip 22.

On this basis, it is then possible to determine a corrected theoretical relationship for variation in the intensity as a function of wavelength, by correcting the approximate theoretical relationship as a function of the linear offset. For example, it is possible merely to subtract point by point the linear offset from the approximate theoretical relationship. Such subtraction thus leads to a corrected curve TC that may be considered to be the portion of the optical response that is associated solely with the characteristic property of the optical agent, e.g. its property of fluorescence.

The corrected curve TC, which may be displayed on a screen for the attention of a user, for example, makes it possible to deduce an intensity peak corresponding to the maximum intensity or corresponding to the mean value of intensity over the width of the peak, which intensity may also be displayed.

It can thus be understood that the chromatic spectral decomposition obtained in this method, as made possible by using a spectrometer in the machine of the invention, enables measurement values of the optical response to be used outside the wavelength range of the characteristic property of the optical agent in order to refine detection in the wavelength range of the characteristic property of the optical agent.

Furthermore, as mentioned above, in the prior art known machines implement methods in which, within a given analysis strip, it is possible to obtain only one analysis because only one optical agent is detected in a given final reaction solution contained in a given analysis zone.

In the invention, a new method is proposed that makes it possible to obtain more information in the context of a single analysis. The method may be implemented by using a machine of the invention that uses a spectrometer as described above.

Like the above-described method, this method may be performed, in particular using a machine of the invention, specifically for the steps of data processing by its central unit or by a remote computer as described above, for automatic in vitro detection and/or quantification of analytes contained in samples. In similar manner to that described above, this method comprises the following steps:

putting the sample into a situation to react with one or more reagents in order to produce directly or indirectly a reaction solution that, when a determined analyte is present in the sample, includes an agent having determined optical properties, in particular fluorescent properties;

illuminating the reaction source with electromagnetic radiation;

detecting the optical response of the reaction solution; and from the optical response, deducing the presence of and/or quantifying the analyte.

In detail, these various steps may be identical or similar to the corresponding steps described in the context of the above method. These details are therefore not repeated here.

This new method implements one or more reagents to produce directly or indirectly a reaction solution that includes at least two distinct optical agents, each having at least one predetermined optical property (color, fluorescence, phosphorescence, . . . , as defined above), each of the two predetermined optical properties corresponding to a respective optical agent being distinct. Thus, the two optical agents may present different colors, different fluorescences, different phosphorescences, . . . all properties that can be distinguished by chromatic spectral decomposition.

The method includes the steps consisting in acquiring a chromatic spectral decomposition of the optical response, and in detecting separately the two distinct predetermined optical properties in said spectral decomposition.

Preferably, the method makes provision for acquiring a single spectral decomposition under given incident electromagnetic radiation. Under such circumstances, the optical properties are detected separately in the sense that they can each be identified in a single spectral decomposition. For example, each optical property may give rise to the presence of an intensity peak having a maximum at a different wavelength. Under such circumstances, the intensity peaks preferably correspond to wavelength ranges that are distinct, and more preferably to ranges that are disjoint.

For example, each optical intensity may present a Gaussian shape.

In a variant, the method makes provision for acquiring a plurality of chromatic spectral decompositions, acquired by illuminating the analysis zone with different incident electromagnetic radiation (differing in particular in terms of chromatic spectral decomposition). Under such circumstances, the distinct predetermined optical properties are detected separately in the sense that each of them can be identified in chromatic spectral decompositions that are distinct.

The step of detecting a predetermined optical property may be performed by detecting the absence of this predetermined optical property.

The method may be implemented to detect the presence of at least two distinct analytes in the sample. Under such circumstances, the various optical agents correspond to distinct analytes. It may also be implemented in order to detect at least two distinct reactions that involve the same analyte. Under such circumstances, the various optical agents correspond to distinct reactions for a single analyte.

In all of the above-described methods, the step consisting in acquiring a chromatic spectral decomposition of the optical response includes a step of chromatically dispersing a light beam coming from the optical response and a step of determining the intensities for components of distinct wavelengths in the beam as dispersed in this way.

Likewise, each of the above methods may include a step of detecting the intensity of the radiation emitted by the source of radiation.

This step may include a step of guiding a fraction of the incident radiation without passing through the analysis zone and a step consisting in acquiring a chromatic spectral decomposition of said fraction of the incident radiation that forms a reference beam, in particular by using spectrometry, as implemented in the device shown in FIG. 5. Under such circumstances, before the step that consists in acquiring a chromatic spectral decomposition of the incident radiation, it is possible to provide a step of mixing said fraction of the incident radiation with the optical response of the reaction solution, e.g. as implemented in the device shown in FIG. 5.

Furthermore, the invention may be improved by using a method and a system as described in Document WO 2013/045807. In that document, there are described a system and a method of modulating the source and of demodulating the detection and reference signals in order to the signal/noise ratio in the detection measurement. The system and the method are described in Document WO 2013/045807 in a context in which there is only one detection signal. The same principle of modulation and detection may be applied in the context of the invention. It is thus possible to modulate the radiation source 58 in amplitude at a frequency/wavelength of the carrier wave. Thereafter, it is possible for the output signal from the spectrometer, which may be analog or digital, and which covers a working range of wavelengths, to be configured into a series of N individual signals, each of which is representative of the signal collected by the spectrometer for an individual wavelength or an individual wavelength range. Preferably, the N individual wavelengths or individual wavelength ranges cover said working wavelength range, preferably in continuous or quasi-continuous manner. For each individual signal, or at least for a preferably representative series of the individual signals, it is possible to perform individually the modulation and demodulation system and method as described in Document WO 2013/045807. By applying that teaching to all of the individual signals, or to a series of those signals, the result is a chromatic spectral decomposition of the optical response that presents a better signal/noise ratio, i.e. a decomposition that is less disturbed by ambient noise in the measurement.

The invention is not limited to the embodiments described and shown, since various modifications may be applied without going beyond its ambit.

Experimental Portion

There follows a description of an experiment showing the capability of a machine and a method of the invention to acquire, in a single acquisition, the optical response corresponding to three optical agents, with the ability to quantify the presence of each optical agent.

In this experiment, three optical agents were used as sold by Thermo Fisher, 3747 N. Meridian Road, PO Box 117, Rockford, Ill. 61105, USA:

Agent A: F(ab')2-Goat anti-Mouse IgG (H+L) Secondary Antibody, Qdot® 605 conjugate;

Agent B: F(ab')2-Goat anti-Mouse IgG (H+L) Secondary Antibody, Qdot® 705 conjugate;

Agent C: F(ab')2-Goat anti-Mouse IgG (H+L) Secondary Antibody, Qdot® 525 conjugate.

The light source used was a monochromatic source emitting in the ultraviolet (370 nm±5 nm) to excite the molecules.

Solutions of agents A, B, and C were prepared using a CHES (N-cyclohexyl-2-aminoethanesulfonic acid) buffer agent, having a pH of 9.2.

Five solutions were prepared:

| | |
|---|---|
| Sol 1 | Agent C 200 nM |
| Sol 2 | Agent A 20 nM |
| Sol 3 | Agent A 200 nM |
| Sol 4 | Agent B 20 nM |
| Sol 5 | Agent A 20 nM |
| | Agent B 20 nM |
| | Agent C 200 nM |

A volume of 250 microliters of each solution was placed in an analysis zone and the optical response of each solution was acquired using a machine of the invention.

Figure 7:
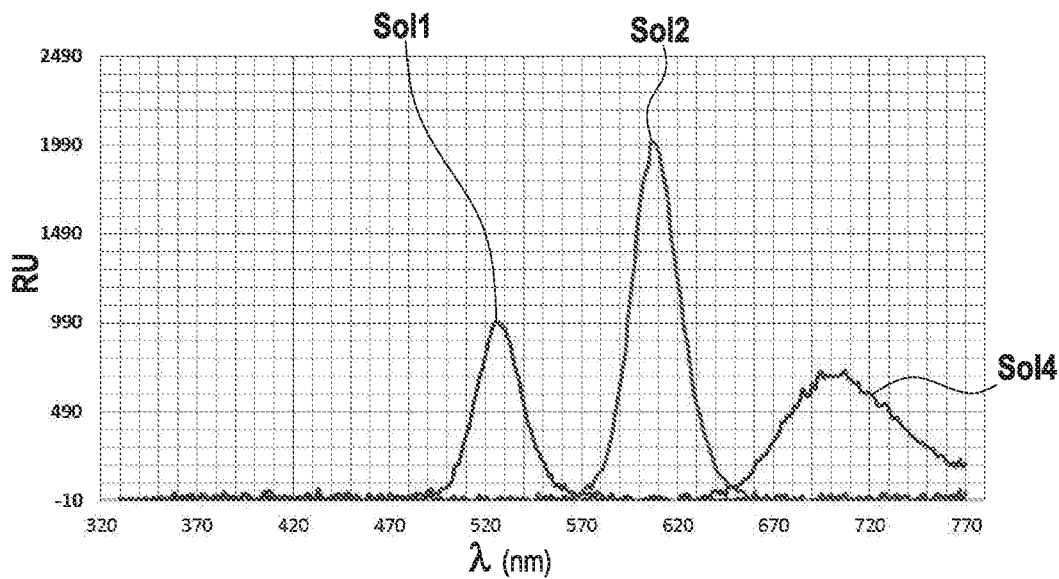
FIG. 7 shows the superposition of three separately-obtained chromatic spectral decompositions for three separate optical agents, as obtained by a method and a device of the invention.

FIG. 7 is a superposition of the spectral decompositions of the optical responses obtained separately for solutions 1, 2, and 4. Each spectral decomposition thus presents a well-identified peak. The curves are expressed in relative intensity units RU for the optical responses as a function of the wavelength ˙ in nm.

Figure 8:
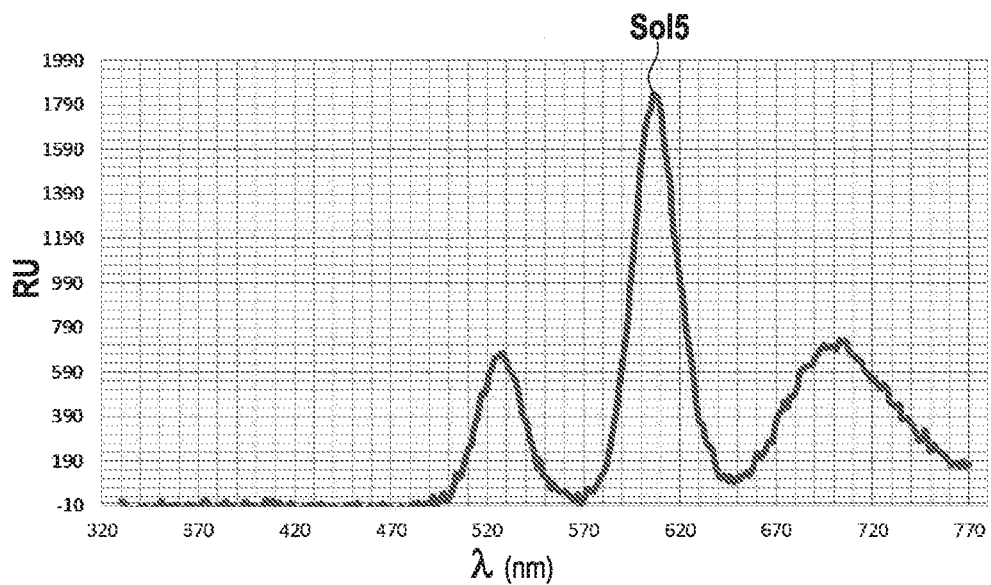
FIG. 8 shows the chromatic spectral decomposition obtained by a method and a device of the invention for a solution that comprises the three optical agents simultaneously.

FIG. 8 shows the spectral decomposition of the optical response obtained separately from the solution 5, comprising a mixture of the three agents. The three peaks can be seen therein, thus revealing the possibility of separately detecting three distinct optical agents in a single analysis.

The curve is expressed in relative intensity units RU of the optical response, as a function of wavelength ˙ in nm.

Using the data from the spectral decomposition shown in FIG. 8, a dynamic Gaussian regression algorithm was applied to discriminate between the responses due to the three optical agents.

Thus, the signal of FIG. 8 was modeled as the sum of three Gaussian functions referred to respectively as G525, G605, and G705, each centered on the fluorescence peak of the corresponding optical agent with:

$$G525(X, A_1, \sigma_1, \mu_1) = A_1 \times \frac{1}{\sqrt{2\pi}\sigma_1} \times e^{-\frac{(X-\mu_1)^2}{2\sigma_1^2}}$$

$$G605(X, A_2, \sigma_2, \mu_2) = A_2 \times \frac{1}{\sqrt{2\pi}\sigma_2} \times e^{-\frac{(X-\mu_2)^2}{2\sigma_2^2}}$$

$$G705(X, A_3, \sigma_3, \mu_3) = A_3 \times \frac{1}{\sqrt{2\pi}\sigma_3} \times e^{-\frac{(X_3-\mu_3)^2}{2\sigma_3^2}}$$

where:
X is the variable, corresponding in this example to wavelength;
A, ˙, and μ are parameters specifying the amplitude, the standard deviation, and the mean value of each Gaussian function.

Thus, the model used for modeling the curve of FIG. 8 showing the spectral decomposition of the optical response obtained separately for solution 5 can be written as the following mixture of Gaussian curves:

$$S(X,A_1,\sigma_1,\mu_1,A_2,\sigma_2,\mu_2,A_2,\sigma_3,\mu_3)=G_{525}(A_1,\sigma_1,\mu_1)+G_{605}(A_2,\sigma_2,\mu_2)+G_{705}(A_3,\sigma_3,\mu_3)$$

The parameter vector to be solved by optimization thus comprises nine parameters:

$$P=(A_1,\sigma_1,\mu,A_2,\sigma_2,\mu_2,A_3,\sigma_3,\mu_3)$$

The optimization process used was the process available in Matlab software by using the algorithm called "flexible simplex method". That algorithm minimizes the cost function constituted by the sum of the squared errors, representing the error between the model (with the instantaneous values of the parameters of the vector for the iteration under consideration) and the experimental curve. On each iteration, the vector P is modified using the algorithm and the sum of the squared errors is verified. The iterations are stopped on reaching an error that is below a given threshold, which depends on the desired accuracy.

The initial values for the parameters used in the optimization process were as follows:

| $A1_0$ | $\sigma1_0$ | $\mu1_0$ | $A2_0$ | $\sigma2_0$ | $\mu2_0$ | $A3_0$ | $\sigma3_0$ | $\mu3_0$ |
|---|---|---|---|---|---|---|---|---|
| 1000 | 525 | 21270 | 170 | 605 | 30270 | 1000 | 705 | 15270 |

These values make it possible to reach a solution quickly, however other initial values could be used.

The result of the optimization gave the following parameters (rounded down to the next integer):

| $\sigma1$ | $\mu1$ | $A1$ | $\sigma2$ | $\mu2$ | $A2$ | $\sigma3$ | $\mu3$ | $A3$ |
|---|---|---|---|---|---|---|---|---|
| 144 | 523 | 19876 | 145 | 603 | 54083 | 988 | 700 | 54574 |

Figure 9:
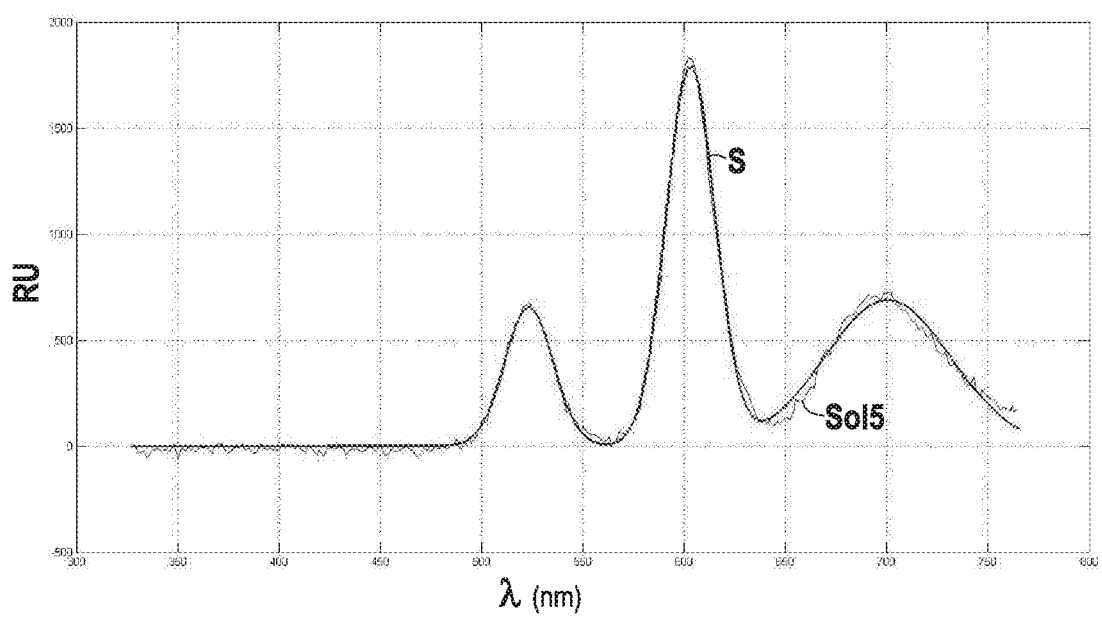
FIG. 9 shows, superposed on the chromatic spectral decomposition of FIG. 8, an overall S-curve for modeling the spectral decomposition of FIG. 8.

FIG. 9 shows the curve of the function S obtained with these optimized parameters superposed on the curve of FIG. 8. The curves are expressed in relative intensity units RU of the optical response, as a function of the wavelength ˙ in nm.

The three functions G525, G605, and G705 as defined with these optimized parameters enable the optical responses due individually to each optical agent to be extracted from the overall optical response shown in FIG. 8. By referring to an appropriate calibration scale, it is easy to quantify the concentration of each optical agent in the single analyzed solution.

Figure 10:
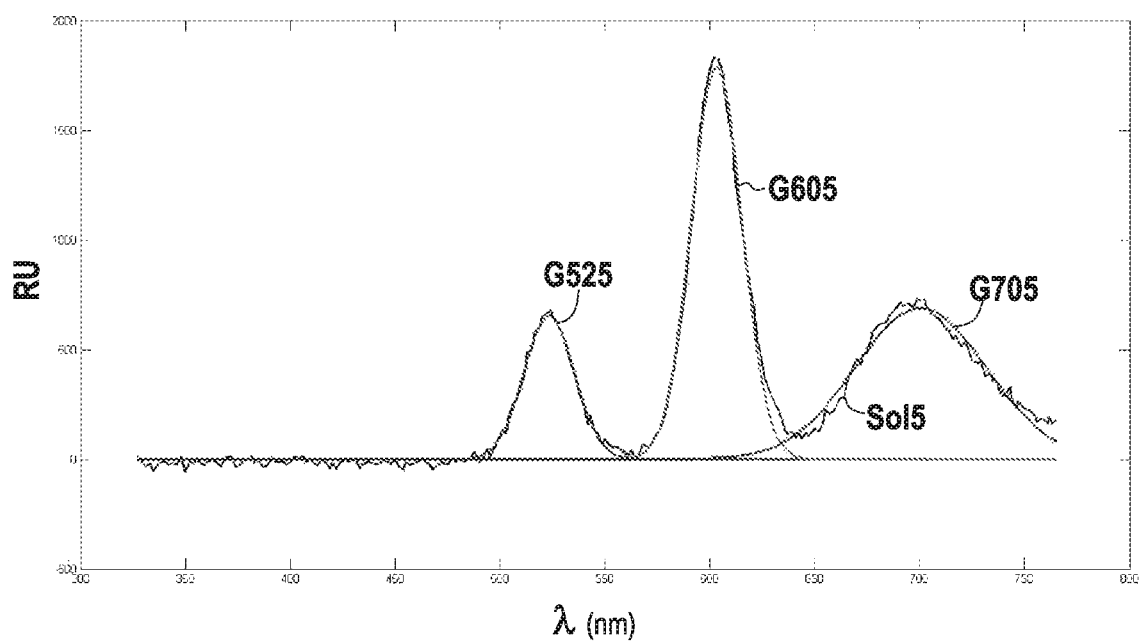
FIG. 10 shows, superposed on the chromatic spectral decomposition of FIG. 8, three curves of components G525, G605, and G705 of the overall modeling S-curve.

FIG. 10 shows the three functions G525, G605, and G705 obtained with these parameters superposed on the curve of FIG. 8. The curves are expressed in relative intensity units RU of the optical response, as a function of wavelength in nm.

This experiment shows how a machine and/or a method of the invention can be implemented to quantify the presence of a plurality of distinct optical agents in a single analysis, which agents may be representative of a plurality of analysis reactions.

In particular:
a laboratory technician or the machine prepares a sample for analysis, which sample may contain a plurality of different types of analyte;
a solution of a plurality of different optical agents presenting distinct optical properties, preferably in optical ranges that are different, e.g. disjoint, are introduced as appropriate into the sample. Each of these agents is specific to a particular type of analyte for which it is desired to discover the presence and/or the concentration/quantity in the sample;
an optical response is measured by the spectrometer for the sample, which response consequently comprises the response of each optical agent if the corresponding analyte is indeed present in the sample, as described above;
the response is communicated to the central unit or to a remote computer, which responds by implementing computer processing to identify the mixture of Gaussian curves that corresponding to the optical agents, in the above-described manner;
as a function of each Gaussian curve of the mixture, the computer processing then determines the concentration and/or the quantity of the corresponding analyte, in the above-described manner; and
the result of the processing may then for example be stored or displayed on a screen.

The invention claimed is:
1. A machine configured to perform automatic in vitro detection and/or quantification of one or more analytes contained in one or more biological samples, the machine comprising:
a plurality of optical analysis zones, each configured to receive a reaction solution obtained by reaction of one or more reagents with a biological sample; and
an optical reader device configured to detect and/or quantify an optical response of the reaction solution to electromagnetic stimulation, the optical reader device comprising:
at least one source of electromagnetic radiation configured to illuminate an analysis zone,
a spectrometer configured to deliver a chromatic spectral decomposition of the optical response, the spectrometer comprising a photoelectric receiver arranged to receive light radiation coming from the reaction solution contained in the illuminated analy- sis zone and configured to detect the optical response of the reaction solution, and a guide system configured to guide a fraction of incident radiation to the spectrometer without passing via the illuminated analysis zone;

wherein:

the photoelectric receiver is carried by a movable carriage of the machine that is motor-driven, and that is moved under automatic control to bring the photoelectric receiver into a plurality of positions, each corresponding to a respective analysis zone; and the optical reader device is further configured to detect an intensity of electromagnetic radiation emitted by the at least one source of electromagnetic radiation by detecting the fraction of incident radiation passed by the guide system to the spectrometer without passing through the illuminated analysis zone.

2. The machine according to claim 1, wherein the spectrometer is configured to deliver the chromatic spectral decomposition of the optical response over at least one working range of wavelengths between two wavelengths $\lambda_{min}$ and $\lambda_{max}$, with $\lambda_{max} \geq 2 \times \lambda_{min}$.

3. The machine according to claim 1, wherein the spectrometer comprises a chromatic dispersion element and the photoelectric receiver is linear or two-dimensional.

4. The machine according to claim 1, wherein the spectrometer comprises an electronic circuit that is connected to the photoelectric receiver, and that delivers an image electrical signal that is an image of the chromatic spectral decomposition of the optical response.

5. The machine according to claim 4, wherein the image electrical signal is an analog signal.

6. The machine according to claim 1, wherein the at least one source of electromagnetic radiation is a monochromatic source.

7. The machine according to claim 1, wherein the at least one source of electromagnetic radiation is a polychromatic source.

8. The machine according to claim 1, wherein:

the one or more reagents comprises an antibody-label conjugate, the at least one source of electromagnetic radiation is configured to emit light to excite the conjugated label and produce the optical response by illuminating the analysis zone, and the spectrometer is configured to deliver a chromatic spectral decomposition of the optical response of the excited conjugated label.

* * * * *